(12) United States Patent
Berry et al.

(10) Patent No.: US 7,628,034 B2
(45) Date of Patent: Dec. 8, 2009

(54) METHOD OF LOW FLOW ANESTHETIC GAS SCAVENGING AND DYNAMIC COLLECTION APPARATUS THEREFOR

(75) Inventors: James M. Berry, Nashville, TN (US); Steve Morris, Canton, MS (US)

(73) Assignee: Anesthetic Gas Reclamation, LLC, Nashville, TN (US)

( * ) Notice: Subject to any disclaimer, the term of this patent is extended or adjusted under 35 U.S.C. 154(b) by 464 days.

(21) Appl. No.: 11/266,966

(22) Filed: Nov. 4, 2005

(65) Prior Publication Data

US 2006/0254586 A1 Nov. 16, 2006

Related U.S. Application Data

(60) Provisional application No. 60/680,644, filed on May 13, 2005.

(51) Int. Cl.
*F25B 3/00* (2006.01)
*F24F 5/00* (2006.01)

(52) U.S. Cl. ............... 62/617; 128/204.16; 128/205.27

(58) Field of Classification Search ............ 128/200.24, 128/205.19, 205.12, 205.27, 204.16, 204.13, 128/202.22, 204.14, 204.15; 62/617
See application file for complete search history.

(56) References Cited

U.S. PATENT DOCUMENTS

| | | | |
|---|---|---|---|
| 575,714 | A | 1/1897 | Heinzerling |
| 1,040,886 | A | 10/1912 | Claude |
| 3,348,538 | A | 10/1967 | Benzel |
| 3,517,521 | A | 6/1970 | Emerson |
| 3,592,191 | A | 7/1971 | Jackson |
| 3,714,942 | A | 2/1973 | Fischel et al. |
| 3,721,239 | A | 3/1973 | Myers |
| 3,800,793 | A | 4/1974 | Marrese et al. |
| 3,867,936 | A | 2/1975 | Kelley |
| 3,941,573 | A | 3/1976 | Chapel |
| 4,004,585 | A | 1/1977 | Boehringer |

(Continued)

FOREIGN PATENT DOCUMENTS

WO          WO 98/08583          3/1998

(Continued)

OTHER PUBLICATIONS

Brown AC, Canosa-Mas CE, Parr AD, et al.: Tropospheric lifetimes of halogenated anaesthetics. Nature 1989; 341: 635-637.

(Continued)

*Primary Examiner*—William C Doerrler
(74) *Attorney, Agent, or Firm*—Gary L. Bush; Mark D. Shelley, II; Andrews Kurth LLP

(57) ABSTRACT

A method and system for removal of nitrous oxide and volatile halocarbon gas components from waste anesthetic gases using a low-flow scavenging or reclamation system preferably including an intelligent waste anesthetic gas collection unit fluidly coupled between each individual anesthetic machine and the waste gas evacuation manifold. Through a system including a collection chamber, a pressure detector, and a exhaust valve which is actuated based on the detected pressure in the collection chamber, the waste anesthetic gas collection unit allows flow to the waste suction manifold only in the presence of waste gas and interrupts all flow into the suction manifold when no waste gas is present.

20 Claims, 5 Drawing Sheets

U.S. PATENT DOCUMENTS

| | | | |
|---|---|---|---|
| 4,127,163 A | | 11/1978 | Reti |
| 4,180,066 A | | 12/1979 | Milliken et al. |
| 4,181,508 A | | 1/1980 | Schmid et al. |
| 4,205,095 A | | 5/1980 | Pike et al. |
| 4,219,020 A | | 8/1980 | Czajka |
| 4,246,015 A | | 1/1981 | Styring |
| 4,259,303 A | | 3/1981 | Nakaji et al. |
| 4,261,178 A | | 4/1981 | Cain |
| 4,265,239 A | | 5/1981 | Fischer, Jr. et al. |
| 4,281,518 A | | 8/1981 | Muller et al. |
| 4,291,689 A | | 9/1981 | Hay |
| 4,312,339 A | | 1/1982 | Thompson, Sr. |
| 4,378,984 A | | 4/1983 | Cheng et al. |
| 4,447,462 A | | 5/1984 | Tafuri et al. |
| 4,451,273 A | | 5/1984 | Cheng et al. |
| 4,527,558 A | | 7/1985 | Hoenig |
| 4,538,605 A | | 9/1985 | Gedeon et al. |
| 4,609,388 A | | 9/1986 | Adler et al. |
| 4,633,890 A | | 1/1987 | Carden |
| 4,653,493 A | | 3/1987 | Hoppough |
| 4,676,239 A | | 6/1987 | Humphrey |
| 4,755,201 A | | 7/1988 | Eschwey et al. |
| 4,768,347 A | | 9/1988 | Manz et al. |
| 4,832,042 A | | 5/1989 | Poppendiek et al. |
| 4,895,172 A | | 1/1990 | Lindkvist |
| 4,905,685 A | | 3/1990 | Olsson et al. |
| 4,928,685 A | | 5/1990 | Gray |
| 4,949,714 A | | 8/1990 | Orr |
| 5,033,464 A | | 7/1991 | Dlcastilho |
| 5,044,361 A | | 9/1991 | Werner et al. |
| 5,044,363 A | | 9/1991 | Burkhart |
| 5,046,491 A | | 9/1991 | Derrick |
| 5,046,492 A | | 9/1991 | Stackhouse et al. |
| 5,062,270 A | | 11/1991 | Haut et al. |
| 5,152,812 A | | 10/1992 | Kovach |
| 5,205,843 A | | 4/1993 | Kaschemekat et al. |
| 5,253,641 A | | 10/1993 | Choate |
| 5,311,862 A | | 5/1994 | Blasdell et al. |
| 5,323,623 A | | 6/1994 | Carns et al. |
| 5,339,642 A | * | 8/1994 | Laukhuf .................. 62/77 |
| 5,345,928 A | | 9/1994 | Lindkvist |
| 5,370,110 A | | 12/1994 | Corn |
| 5,398,675 A | | 3/1995 | Henkin et al. |
| 5,419,317 A | | 5/1995 | Blasdell et al. |
| 5,450,728 A | | 9/1995 | Vora et al. |
| 5,482,033 A | | 1/1996 | Engle et al. |
| 5,507,282 A | | 4/1996 | Younes |
| 5,520,169 A | | 5/1996 | Georgieff et al. |
| 5,568,910 A | | 10/1996 | Koehler et al. |
| 5,676,133 A | | 10/1997 | Hickle et al. |
| 5,678,540 A | * | 10/1997 | Kock et al. .............. 128/205.13 |
| 5,694,924 A | | 12/1997 | Cewers |
| 5,715,813 A | | 2/1998 | Guevrekian |
| 5,740,682 A | | 4/1998 | Lavie |
| 5,759,504 A | | 6/1998 | Kanno et al. |
| 5,769,072 A | | 6/1998 | Olsson et al. |
| 5,819,555 A | | 10/1998 | Engdahl |
| 5,928,411 A | | 7/1999 | Falb et al. |
| RE36,460 E | | 12/1999 | Klatz et al. |
| 6,030,591 A | | 2/2000 | Tom et al. |
| 6,076,524 A | | 6/2000 | Corn |
| 6,080,226 A | | 6/2000 | Dolan et al. |
| 6,082,133 A | | 7/2000 | Barclay et al. |
| 6,131,571 A | * | 10/2000 | Lampotang et al. ..... 128/204.21 |
| 6,134,914 A | * | 10/2000 | Eschwey et al. ............... 62/637 |
| 6,158,434 A | | 12/2000 | Lugtigheid et al. |
| 6,206,002 B1 | | 3/2001 | Lambert |
| 6,237,596 B1 | | 5/2001 | Bohmfalk |
| 6,328,036 B1 | * | 12/2001 | Emtell et al. ........... 128/205.14 |
| 6,357,437 B1 | | 3/2002 | Jacques |
| 6,374,635 B1 | | 4/2002 | Hayakawa et al. |
| 6,405,539 B1 | * | 6/2002 | Stach et al. .................... 62/3.4 |
| 6,475,266 B2 | | 11/2002 | Hayashi et al. |
| 6,488,028 B1 | | 12/2002 | Lambert |
| 6,490,883 B2 | | 12/2002 | Trembley et al. |
| 6,513,345 B1 | | 2/2003 | Betting et al. |
| 6,536,430 B1 | | 3/2003 | Smith |
| 6,729,329 B2 | * | 5/2004 | Berry ..................... 128/204.16 |
| 6,736,140 B1 | | 5/2004 | Baczkowski |
| 6,776,158 B1 | | 8/2004 | Anderson et al. |
| 6,863,067 B2 | | 3/2005 | Loncar |
| 2003/0185735 A1 | | 10/2003 | Hotta et al. |
| 2005/0155380 A1 | | 7/2005 | Rock |
| 2006/0254587 A1 | | 11/2006 | Berry et al. |
| 2006/0254589 A1 | | 11/2006 | Berry et al. |
| 2006/0254590 A1 | | 11/2006 | Berry et al. |

FOREIGN PATENT DOCUMENTS

| | | |
|---|---|---|
| WO | WO 01/24858 | 4/2001 |

OTHER PUBLICATIONS

Langbein T, Sonntag H, Trapp D, et al.: Volatile anaesthetics and the atmosphere: atmospheric lifetimes and atmospheric effects of halothane, enflurane, isoflurane, desflurane and sevoflurane. Br J Anaesth 1999; 82: 66-73.

McCulloch, A.: Letter to Editor regarding Langbein, et al. 1999 paper. Br J Anaesth 2000; 84 (4): 534-36.

Dunn, R.F., M. Zhu, B.K. Srinivas and M. M. El-Halwagi (1995), Optimal Design of Energy-Induced Separation Networks for VOC Recovery, AIChE Symp. Ser., 90(303), 74-85, NY: AIChE.

Written Opinion of International Search Authority for PCT/US2006/18416 mailed on Sep. 24, 1007.

Examiner's First Office Action mailed Oct. 10, 2008 in connection with U.S. Appl. No. 11/432,192.

Applicant's Response to First Office Action filed Apr. 9, 2009 in connection with U.S. Appl. No. 11/432,192.

Applicant's Supplemental Response to First Office Action filed Apr. 10, 2009 in connection with U.S. Appl. No. 11/432,192.

Examiners's First Office Action mailed Oct. 15, 2008 in connection with U.S. Appl. No. 11/432,152.

Applicant's Response to First Office Action filed Apr. 14, 2009 in connection with U.S. Appl. No. 11/432,152.

Examiner's First Office Action mailed Oct. 10, 2008 in connection with U.S. Appl. No. 11/432,189.

Applicant's Response to First Office Action filed Apr. 10, 2009 in connection with U.S. Appl. No. 11/432,189.

Applicant's Supplemental Response to First Office Action filed Apr. 10, 2009 in connection with U.S. Appl. No. 11/432,189.

Examiner's Final Office Action mailed May 4, 2009 in connection with U.S. Appl. No. 11/432,192.

Notice of Allowance dated May 20, 2009 in connection with U.S. Appl. No. 11/432,189.

Examiner's non-final Office Action mailed Jun. 1, 2009 in connection with U.S. Appl. No. 11/432,152.

* cited by examiner

US 7,628,034 B2

METHOD OF LOW FLOW ANESTHETIC GAS SCAVENGING AND DYNAMIC COLLECTION APPARATUS THEREFOR

CROSS REFERENCE TO RELATED APPLICATION

This application is based upon provisional application 60/680,644 filed on May 13, 2005, the priority of which is claimed. On May 11, 2006, Applicants filed non-provisional application Ser. No. 11/432,152, which claims the benefit of U.S. provisional patent application 60/680,644 filed on May 13, 2005. On May 11, 2006, Applicants filed non-provisional application Ser. No. 11/432,192, which claims the benefit of U.S. provisional patent application 60/680,644 filed on May 13, 2005. On May 11, 2006, Applicants filed non-provisional application Ser. No. 11/432,189, which claims the benefit of U.S. provisional patent applications 60/680,644 filed on May 13, 2005 and 60/682,249 filed on May 18, 2005.

BACKGROUND OF THE INVENTION

1. Field of the Invention

This invention concerns treatment of waste anesthetic gases from healthcare or other facilities that use inhaled anesthetics for medical or veterinary purposes. In particular, the invention pertains to the removal and reclamation of nitrous oxide, flouroethers, and other halocarbons from a stream of waste anesthetic gases produced by one or more anesthesia delivery systems of a healthcare facility in order to reduce atmospheric pollution before the gas stream is discharged to the atmosphere.

2. Description of the Prior Art

Anesthesia delivery systems in surgical facilities (both hospital and outpatient) produce significant quantities of waste anesthetic gases. Currently these gases are collected from the patients' exhalation by a dedicated or shared vacuum system. The healthcare facilities typically employ one or more centrally-located vacuum pumps to collect waste gases from individual anesthetizing locations. These vacuum pumps are usually oversized, because they are designed to collect exhaled anesthetics over a wide range of flows. Because these pumps operate continuously, the waste anesthetic gas suction system also entrains large amounts of surrounding room air from the anesthetizing locations, significantly diluting the waste anesthetic gases therein. At the central vacuum pump(s), the gas stream is often admixed with additional room air to further dilute it prior to its ejection from the facility. This dilute waste anesthetic gas/air mixture is typically pumped to the outside of the medical facility, where it is vented to the atmosphere.

The waste anesthetic gases are generally collected at about 20-30° C. with relative humidity ranging between 10 to 60 percent. The average composition of the waste gases is estimated to be (in percent volume) 25-32 percent oxygen, 60-65 percent nitrogen, 5-10 percent nitrous oxide, and 0.1-0.5 percent volatile halocarbons, including flouroethers such as isoflurane, desflurane and sevoflurane. The waste anesthetic gas may also contain trace lubricating oil vapor from vacuum pumps. Like Freon-12® and similar refrigerants, waste anesthetic gas halocarbons (primarily halogenated ethers) contribute to ozone depletion and environmental warming, and they represent an increasingly significant source of environmental concern. Although waste anesthetic gas emissions have thus far escaped environmental regulation in the United States, it is likely that legislative initiatives for ultimate strict regulation of waste anesthetic gas emissions will occur in the near future.

Several techniques have been proposed to treat waste anesthetic gases in an attempt to remedy the growing problem of waste anesthetic gas emissions. For example, U.S. Pat. No. 4,259,303 describes the treatment of laughing gas with a catalyst, U.S. Pat. No. 5,044,363 describes the adsorption of anesthetic gases by charcoal granules, U.S. Pat. No. 5,759,504 details the destruction of anesthetic gases by heating in the presence of a catalyst, U.S. Pat. No. 5,928,411 discloses absorption of anesthetic gases by a molecular sieve, and U.S. Pat. No. 6,134,914 describes the separation of xenon from exhaled anesthetic gas. A cryogenic method for scrubbing volatile halocarbons from waste anesthetic gas is taught by Berry in U.S. Pat. No. 6,729,329, which is incorporated herein by reference.

FIG. 1 illustrates a typical waste anesthetic gas reclamation system (10) of prior art for a healthcare facility. The system (10) includes a number of individual anesthetizing stations (15A, 15B, 15C), each having an anesthetizing machine (12A, 12B, 12C) which delivers anesthesia to a patient via a mask (14A, 14B, 14C) or similar device. Excess anesthetic gases, patients' exhalation, and air are collected at the masks (14A, 14B, 14C) by the anesthetizing machines (12A, 12B, 12C) and discharged to a common collection manifold (16). The waste anesthetic gas collection manifold is typically hard plumbed into the healthcare facility, and the anesthetizing machines (12A, 12B, 12C) are removably connected to the collection manifold (16) at standard waste anesthetic gas connectors (18A, 18B, 18C), e.g. 19 mm or 30 mm anesthetic connectors. The waste anesthetic gas collection system (10) operates at a vacuum pressure which is generated by one or more central vacuum pumps (20). The collected waste gas stream is typically passed through one or more heat exchanger condensers (22). A source of liquid oxygen, or other suitable heat sink, extracts heat from the waste anesthetic stream, condensing the anesthetic gas components. The liquid waste anesthetic condensate is captured in a collection vessel (24). The remaining gas stream, stripped of waste anesthetic gas components, passes through a receiver (26) and the vacuum pump(s) (20), and it is then exhausted to the atmosphere outside of the healthcare facility.

The current methods for scavenging waste anesthetic gases from anesthetizing locations (15A, 15B, 15C) in healthcare facilities generally involve drawing high flows of room air into the dedicated or shared vacuum collection manifold (16) to entrain waste anesthetic gases. The collection manifold (16) may also continuously draw in air through a number of idle anesthetizing machines (12A, 12B, 12C). On average, the collection system manifold (16) extracts between 20-30 liters of waste anesthetic gas and/or room air per minute at each anesthetizing location (15A, 15B, 15C). For a large hospital having between 20-30 operating rooms, it is estimated that waste anesthetic reclamation system (10) flow rate ranges between 500-1000 l/min. (14-35 scf/min.).

The advantages of a high-flow dilute waste gas system are that the system easily accommodates a wide range of anesthetic exhaust flows, the system is safe, in that little anesthetic can escape the system, and the system is simple, requiring little maintenance. However, high-flow systems are energy-intensive, generally requiring large vacuum pumps (20) in order to maintain sufficient suction at a large number of anesthetizing stations (15A, 15B, 15C). For example, to maintain a vacuum of about 200 mm Hg at a flow rate of 1-2 cfm at each anesthetizing station (15A, 15B, 15C), vacuum pumps of 100-200 cfm capacity are common. Furthermore, because removal of a waste component by condensation requires lowering the temperature of the flow stream to a point where the partial pressure of the waste component is equal to or greater than its saturated vapor pressure (at that temperature), diluted waste anesthetic gas concentrations can hamper efficient recovery by condensation processes. A method and system for increasing the efficacy and efficiency of condensation-type waste anesthetic gas scavenging and reclamation systems is thus desirable.

3. Identification of Objects of the Invention

A primary object of the invention is to provide an economical system and method for removing flouroethers and other volatile halocarbons from waste anesthetic gases from a surgical or other healthcare facility before such gases are vented to the atmosphere.

Another object of the invention is to provide an economical system and method for removing nitrous oxide from waste anesthetic gases from a surgical or other healthcare facility before such gases are vented to the atmosphere.

Another object of the invention is to provide an economical system and method for substantially preventing atmospheric venting of flouroethers and other volatile halocarbons of waste anesthetic gas while eliminating the need of prior art catalysts, charcoal granules and heating techniques.

Another object of the invention is to provide an economical system and method for increasing the efficacy and efficiency of condensation-type waste anesthetic scavenging systems.

Another object of the invention is to provide an economical system and method which utilizes and enhances existing waste anesthetic gas reclamation systems of healthcare facilities for minimal impact and cost.

Another object of the invention is to provide a system and method which requires minimal additional investment for a healthcare facility to implement.

Another object of the invention is to provide a system and method which reclaims and allows re-distillation and/or reuse of a large percentage of the nitrous oxide and/or anesthetic halocarbon used in the facility.

Another object of the invention is to provide a system and method which reduces anesthetic-related halocarbon emissions from a healthcare facility into the atmosphere by about 99 percent or more.

SUMMARY OF THE INVENTION

The objects identified above, as well as other advantages and features are preferably embodied in a system and method for removal of nitrous oxide and volatile halocarbon gas components from waste anesthetic gases using a low-flow scavenging or reclamation system which in a preferred embodiment includes a number of intelligent waste anesthetic gas collection units, one located at each individual anesthetizing machine in a healthcare or surgical facility which are fluidly coupled to a combined collection manifold. Each intelligent gas collection unit includes a collection chamber, an exhaust valve to selectively isolate the suction of the collection manifold at the respective anesthetizing station when waste anesthetic gas is not being produced, and associated sensors, circuitry, controls, or mechanisms to operate the exhaust valve.

Waste anesthetic gas enters from the anesthetizing machine exhaust into the collection chamber 32 through a standard anesthetic waste-gas connector. Located within the collection chamber is a sensitive pressure sensor which is preferably electrically coupled to a solenoid-operated exhaust valve located at the exhaust side of the collection chamber. The pressure measured by the pressure sensor is the difference between the pressure of the collection chamber and the outside ambient air pressure. If the pressure within the collection chamber exceeds ambient pressure, the increased pressure is detected by the pressure sensor, which by control circuitry causes the exhaust valve to open and results in a rapid decrease in collection chamber pressure. As the chamber pressure approaches ambient, the pressure sensor detects the pressure drop and causes the exhaust valve to shut.

The collection circuitry is preferably a low voltage direct current circuit, and the exhaust valve is preferably configured as a normally-open valve. A mechanical vacuum breaker and a mechanical relief valve exist in the collection chamber for safety purposes.

The pressure detector, exhaust valve, and the circuitry therebetween may optionally be selected and designed to provide a proportional response to pressure changes, so that the exhaust valve opens a small amount for a small pressure rise and a larger amount for a larger pressure rise. In alternate embodiments, the pressure sensor may be pneumatically or mechanically coupled to the exhaust valve for control thereof, and/or the intelligent waste anesthetic gas collection unit may be incorporated into an improved anesthetizing machine instead of integrated with the healthcare facility waste anesthetic gas collection manifold. The improved anesthetizing machine thus includes the anesthetizing machine of prior art and an intelligent waste anesthetic gas collection unit according to an embodiment of the invention.

Isolating the collection manifold from entraining room air when no waste anesthetic gas is being produced reduces the average anesthetic scavenging flow by approximately 90 percent, thus reducing the necessary capacity of the vacuum pumps, piping, and associated other hardware.

BRIEF DESCRIPTION OF THE DRAWINGS

The invention is described in detail hereinafter on the basis of the embodiments represented in the accompanying figures, in which.

DESCRIPTION OF THE PREFERRED EMBODIMENT OF THE INVENTION

Figure 1:
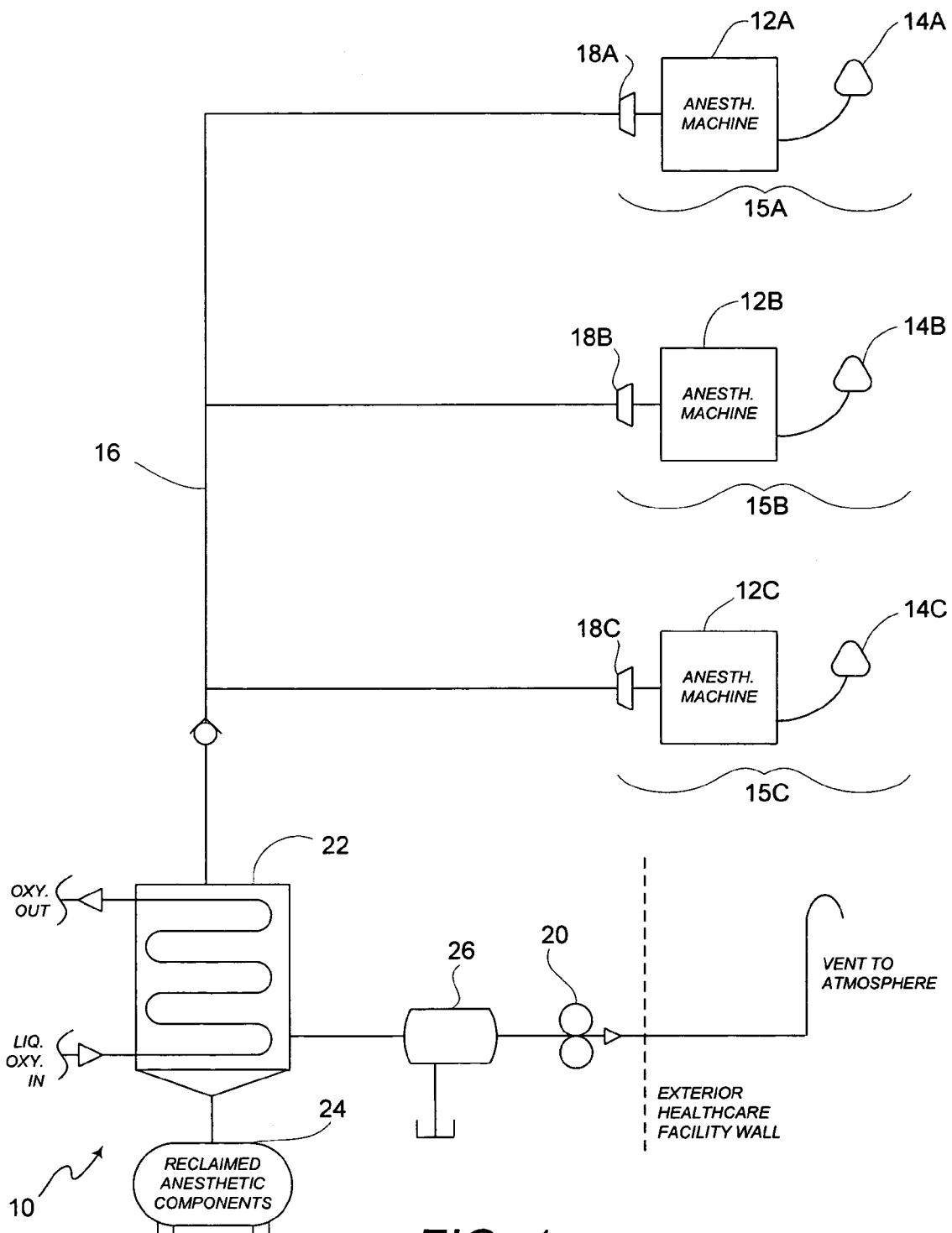
FIG. 1 illustrates in schematic form a high-flow waste anesthetic gas reclamation system of prior art by which flouroethers and other volatile halocarbon gas components of waste anesthetic gases are separated from the collected gas stream by condensation before venting to the atmosphere.
Figure 2:
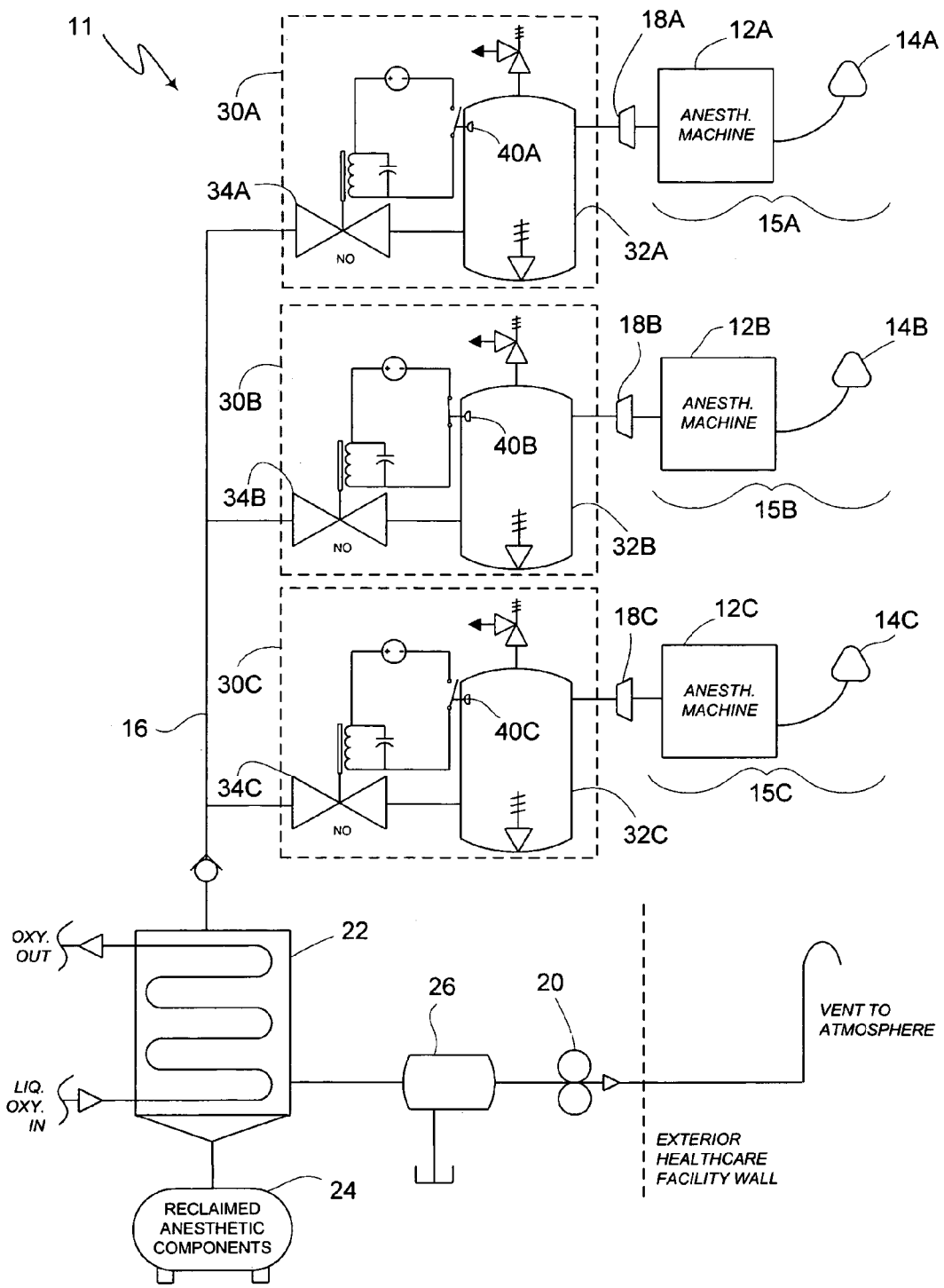
FIG. 2 illustrates in schematic form a preferred embodiment of a low-flow waste anesthetic gas reclamation system according to the invention including intelligent waste anesthetic gas collection units which limit air evacuation into the combined vacuum system.

FIG. 2 schematically illustrates a preferred embodiment of the low-flow waste anesthetic gas collection and reclamation system 11 according to the invention. The reclamation system 11 is nearly identical to the prior art waste reclamation system 10 of FIG. 1 described above except for the inclusion of intelligent waste anesthetic gas collection units 30A, 30B, 30C located at or near each anesthetizing station 15A, 15B, 15C in the healthcare facility. The intelligent waste anesthetic gas collection units 30A, 30B, 30C are preferably fluidly coupled within the individual legs of the collection manifold 16 near the standard waste anesthetic gas connectors 18A, 18B, 18C. Each intelligent gas collection unit 30A, 30B, 30C includes a collection chamber 32A, 32B, 32C, an exhaust valve 34A, 34B, 34C to selectively isolate the suction of the collection manifold 16 at the respective anesthetizing station when waste anesthetic gas is not being produced, and associated sensors, circuitry, controls, or mechanisms to operate the exhaust valve 34A, 34B, 34C. The collection chambers 32 may be rigid, flexible (such as an elastic bag), or a combination of both.

Isolating the collection manifold 16 from entraining room air when no waste anesthetic gas is being produced reduces the average anesthetic scavenging flow by approximately 90 percent, thus reducing the necessary capacity of the vacuum pumps, piping, and associated other hardware. Thus, for a large hospital having between 20-30 operating rooms, it is estimated that waste anesthetic gas flow rate of 500-1000 l/min with the prior art reclamation system 10 of FIG. 1 is reduced to 50-100 l/min with the reclamation system 11 of FIG. 2 according to the preferred embodiment of the invention. The reclamation system 11 described above requires only the addition of individual intelligent waste anesthetic gas collection units 30A, 30B, 30C to an already existing healthcare waste anesthetic gas reclamation system 10, thus providing a simple and inexpensive means for upgrading current systems.

Figure 3:
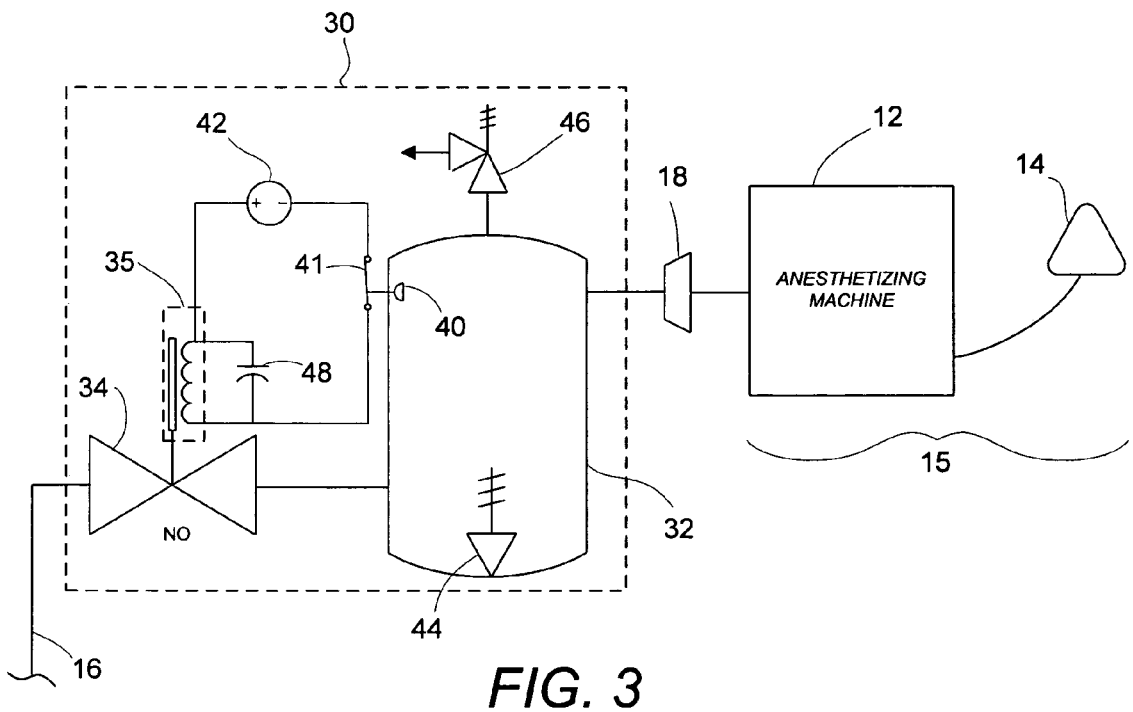
FIG. 3 is a detailed schematic drawing of an intelligent waste anesthetic gas collection unit of FIG. 2 showing a collection chamber at ambient pressure and a pressure detector with associated circuitry to position a solenoid-operated exhaust valve in the shut position.

FIG. 3 illustrates an individual intelligent waste anesthetic gas collection unit 30 according to a preferred embodiment of the invention. Referring to FIG. 3, waste anesthetic gas enters from the anesthetizing machine 12 exhaust into a chamber 32 through a 19 mm, 30 mm, or similar, standard anesthetic waste-gas connector 18. Within the chamber 32 is a sensitive pressure sensor 40 electrically coupled to a solenoid-operated exhaust valve 34 located at the exhaust side of the chamber 32. The pressure measured by pressure sensor 40 is the difference between the pressure of chamber 32 and the outside (ambient) air pressure. If the pressure within the chamber 32 rises to slightly above ambient, the increased pressure is detected by the pressure sensor 40, which by control circuitry causes the exhaust valve 34 to open. Opening valve 34 fluidly connects the chamber 32 to the vacuum source in collection manifold 16, resulting in a rapid decrease in pressure in chamber 32. As the chamber pressure approaches ambient, the sensor 40 detects the pressure drop and causes the exhaust valve 34 to close. In the preferred embodiment, the intelligent waste anesthetic gas collection unit 30 is powered electrically by a direct current low voltage source 42 to minimize the hazard of fire or explosion.

Preferably, exhaust valve 34 is configured as a normally-open valve, so that if a fault occurs, the exhaust valve 34 will fail open, and the system will, in effect, revert to the a continuous-flow air-dilution scavenging system of prior art. Moreover, a means of preventing excessive positive or negative pressures being transmitted to the anesthetizing machine 12 is provided in anesthetic waste gas collection unit 30 to assure patient safety. Although unlikely, should exhaust valve 34 leak by its seat or stick in the open position causing the pressure in chamber 32 to decrease significantly below ambient, a mechanical vacuum breaker 44 exists in chamber 32 which will be drawn open to restore the pressure to ambient. Similarly, should the pressure in chamber 32 increase significantly above ambient, a mechanical relief valve 46 will open to vent the excess pressure to the atmosphere. The waste anesthetic gas collection unit 30 is preferably constructed of materials which comply with safety standards for use in oxygen-enriched environments.

Figure 4:
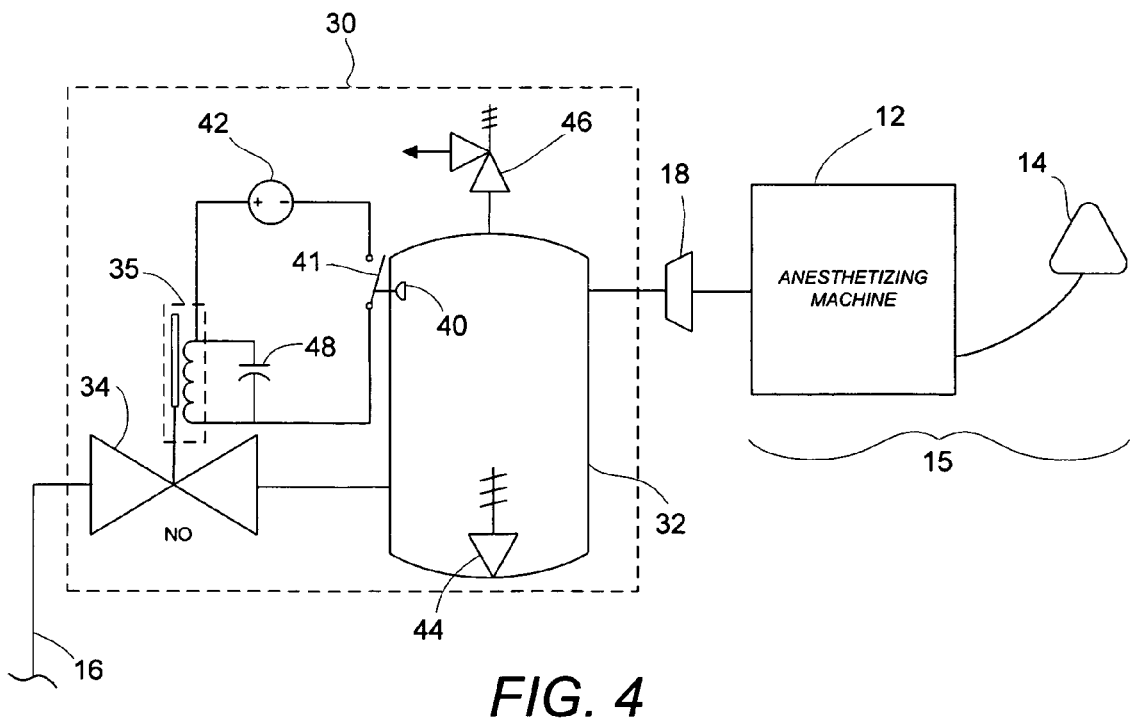
FIG. 4 is a detailed schematic drawing of the intelligent waste anesthetic gas collection unit of FIG. 3 wherein the collection chamber is at a pressure slightly greater than ambient pressure and the pressure detector and associated circuitry are operating to position the solenoid-operated exhaust valve in the open position.

Referring to FIGS. 3 and 4, voltage source 42 is preferably wired in series with the switch contacts 41 of pressure detector 40 and with the solenoid 35 of exhaust valve 34. A damping capacitor 48 may optionally be wired in parallel with the exhaust valve solenoid 35. As illustrated in FIG. 3, when the pressure in chamber 32 is near ambient pressure, the contacts 41 of pressure detector 40 are closed, and current flows between voltage source 42 and solenoid 35, energizing solenoid 35 and shutting exhaust valve 34. When the pressure in chamber 32 increases slightly above ambient, as illustrated in FIG. 4, the contacts 41 of pressure detector 40 are opened, thus de-energizing solenoid 35 and allowing exhaust valve 34 to open. The circuitry illustrated in FIGS. 3 and 4 is of the simplest design, but other more sophisticated circuits may also be used. For example, pressure detector 40, exhaust valve 34, the circuitry therebetween may be selected and designed to provide a proportional response to pressure changes, so that valve 34 opens a small amount for a small pressure rise and a larger amount for a larger pressure rise. Alternatively, suitable means for detecting exhaled breath other than by pressure increases, such as by detection of halocarbons, moisture, or flow, may be used. As both the selection and design of pressure detectors, power supplies, and electrically actuated valves and basic electrical circuit design are well known in the art, further discussion of these topics is not provided herein.

Although FIG. 3 illustrates an electrical circuit coupling pressure sensor 40 and exhaust valve 34, the pressure sensor 40 may alternatively be pneumatically or mechanically coupled to exhaust valve 34 for control thereof. The selection and design of mechanical pressure-controlled actuators, mechanically operated valves, pneumatic control circuits, and pneumatically actuated valves is well known in the art; therefore, further discussion is not provided herein.

Figure 5:
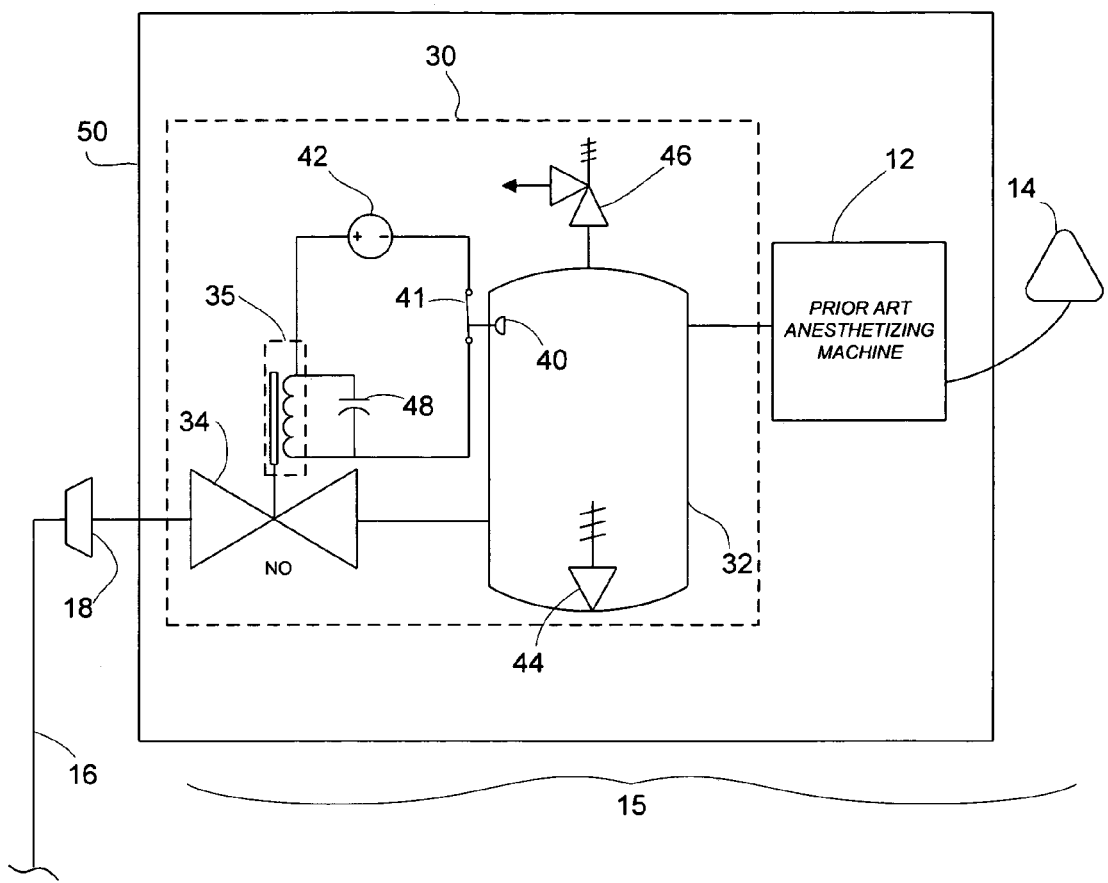
FIG. 5 illustrates in schematic form an alternate embodiment of a low-flow waste anesthetic gas reclamation system wherein an intelligent waste anesthetic gas collection unit is combined with an anesthetizing machine of prior art to form an improved anesthetizing machine.

In an alternate embodiment, illustrated in FIG. 5, the intelligent waste anesthetic gas collection unit 30 may be incorporated into an improved anesthetizing machine 50 instead of integrated with the healthcare facility waste anesthetic gas collection manifold 16. The improved anesthetizing machine 50 thus includes the anesthetizing machine 12 of prior art and an intelligent waste anesthetic gas collection unit 30 according to an embodiment of the invention as set forth herein. The improved anesthetizing machine 50 is removably coupled to a 19 mm, 30 mm, or similar, standard anesthetic waste-gas connector 18. A healthcare facility having a waste anesthetic gas reclamation system equipped with improved anesthetizing machines 50 at all anesthetizing stations 15 will perform in the same manner as the waste anesthetic gas reclamation system 11 of FIG. 2.

Figure 6:
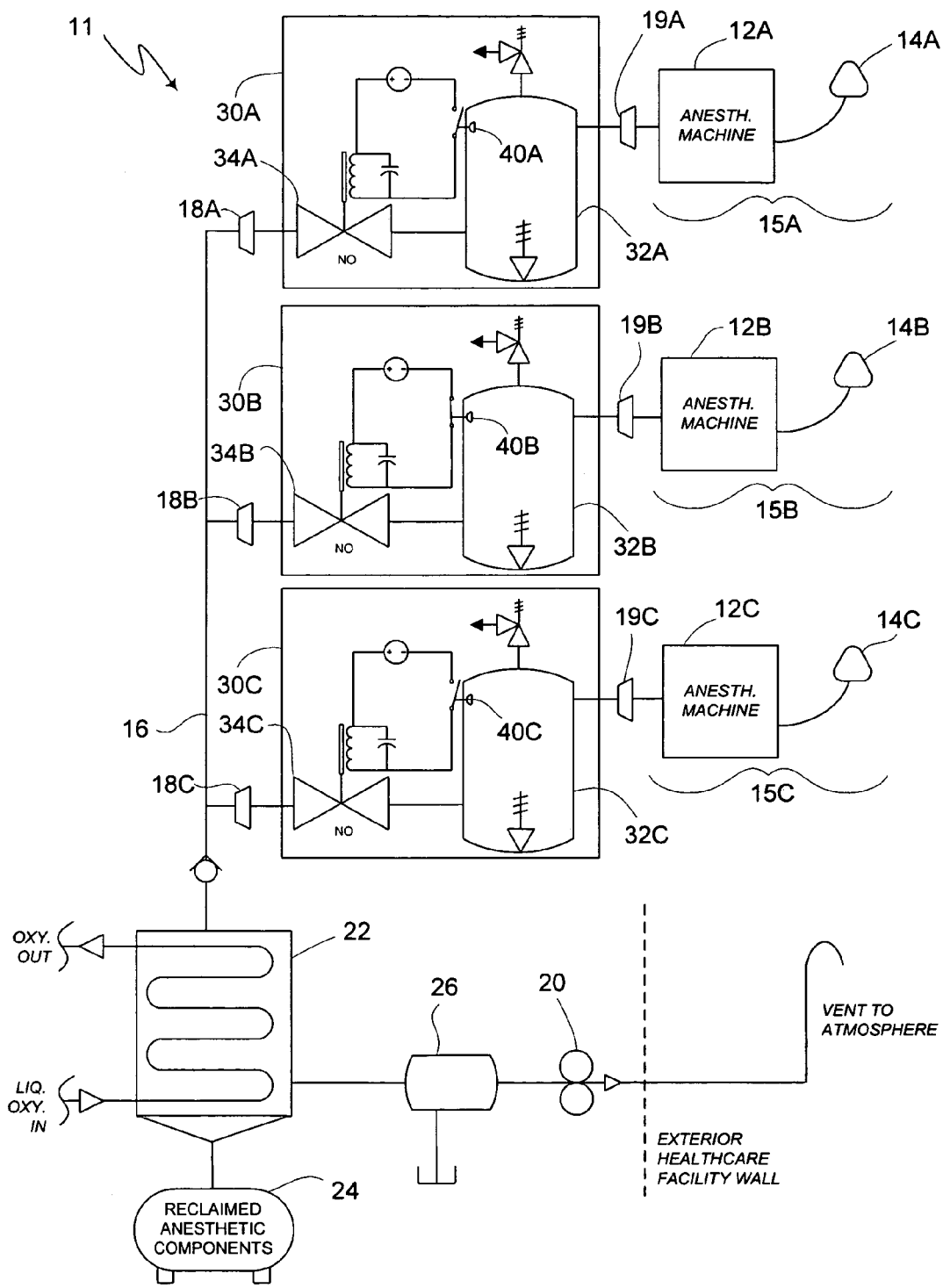
FIG. 6 illustrates in schematic form an alternate embodiment of a low-flow waste anesthetic gas reclamation system useful for retrofitting existing systems wherein intelligent anesthetic gas collection units are separate and distinct from both the collection manifold and from the anesthetizing machine.

FIG. 6 illustrates an alternate embodiment where collection units 30A, 30B, 30C are separate and distinct from both the collection manifold 16 and the anesthetizing machines 12A, 12B, 12C. In this embodiment, each collection unit 30A, 30B, 30C removably connects to manifold 16 at a first standard (e.g., 19 mm or 30 mm) anesthetic waste gas connector 18A, 18B, 18C. Each anesthetizing machine 12A, 12B, 12C is in turn removably connected to a second standard anesthetic waste gas connector 19A, 19B, 19C. Thus, neither modification of the collection manifold 16 nor modification of the anesthetizing machines 12A, 12B, 12C is required to upgrade an existing waste anesthetic gas scavenging system to a low-flow reclamation system according to the invention.

The Abstract of the disclosure is written solely for providing the United States Patent and Trademark Office and the public at large with a means by which to determine quickly from a cursory inspection the nature and gist of the technical disclosure, and it represents solely a preferred embodiment and is not indicative of the nature of the invention as a whole.

While some embodiments of the invention have been illustrated in detail, the invention is not limited to the embodiments shown; modifications and adaptations of the above embodiment may occur to those skilled in the art. Such modifications and adaptations are in the spirit and scope of the invention as set forth herein:

The invention claimed is:

1. An apparatus (30) for collection of waste anesthetic gases comprising:
    a first chamber (32A) having an input and an output in fluid communication with each other, said input of said first chamber fluidly coupled to an exhaust of a first anesthetizing machine (12A) and arranged to receive a gas stream therefrom which includes a waste anesthetic gas component;
    a first exhaust valve (34A) having a first end fluidly coupled to said output of said first chamber and having a second end adapted to be fluidly coupled to a vacuum manifold (16), said first exhaust valve designed and arranged to selectively isolate said first chamber from said vacuum manifold; and
    a first detector (40A) coupled to said first chamber which is designed and arranged to detect said gas stream including said waste anesthetic gas component exiting said first anesthetizing machine by determining when said gas stream including said waste anesthetic gas component enters and is present in said first chamber, said first detector operatively coupled to said first exhaust valve for control thereof; whereby
    when said first detector determines that said gas stream including said waste anesthetic gas component enters and is present in said first chamber, said first detector causes said first exhaust valve to open to fluidly connect said output of said first chamber to said vacuum manifold for evacuation of said gas stream including said waste anesthetic gas component from said first chamber into said vacuum manifold, and
    when said first detector detects that no gas stream including said waste anesthetic gas component is exiting said first anesthetizing machine, said first detector causes said first exhaust valve to be closed.

2. The apparatus of claim 1 wherein:
said first detector is a pressure detector.

3. The apparatus of claim 1 wherein:
said first exhaust valve is a solenoid-actuated valve.

4. The apparatus of claim 1 further comprising:
a mechanical relief valve (46) fluidly coupled to said first chamber.

5. The apparatus of claim 1 further comprising:
a mechanical vacuum breaker (44) fluidly coupled to said first chamber.

6. The apparatus of claim 1 wherein:
said first detector is operatively coupled to said first exhaust valve by a direct current low voltage electrical circuit.

7. The apparatus of claim 1 further comprising:
a vacuum manifold (16) fluidly coupled to said second end of said first exhaust valve (34A); and
a waste anesthetic gas scavenging device (22, 24, 26, 20) fluidly coupled to said vacuum manifold for receiving said gas stream therefrom, said waste anesthetic gas scavenging device designed and arranged to remove said waste anesthetic gas component from said gas stream.

8. The apparatus of claim 7 wherein:
said waste anesthetic gas scavenging device includes a condenser (22) and a cryogenic heat sink, said cryogenic heat sink causing condensation of said waste anesthetic gas component from said gas stream in said condenser.

9. The apparatus of claim 1 further comprising:
a vacuum manifold (16) fluidly coupled to said second end of said first exhaust valve (34A);
first and second anesthetizing machines (12A, 12B) each having an exhaust, said input of said first chamber (32A) being fluidly coupled to said exhaust of said first anesthetizing machine (12A);
a second chamber (32B) having an input and an output, said input of said second chamber fluidly coupled to said exhaust of said second anesthetizing machine (12B) and arranged to receive another gas stream therefrom;
a second exhaust valve (34B) having a first end fluidly coupled to said output of said second chamber (32B) and having a second end fluidly coupled to said vacuum manifold, said second exhaust valve designed and arranged to selectively isolate said second chamber from said vacuum manifold; and
a second detector (40B) coupled to said second chamber which is designed and arranged to detect said another gas stream exiting said second anesthetizing machine by determining when said another gas stream enters and is present in said second chamber, said second detector operatively coupled to said second exhaust valve for control thereof; whereby
when said second detector determines that said another gas stream enters and is present in said second chamber, said second detector causes said second exhaust valve to open to fluidly connect said output of said second chamber to said vacuum manifold for evacuation of said another gas stream from said second chamber into said vacuum manifold,
when said second detector detects that no gas stream is exiting said second anesthetizing machine, said second detector causes said second exhaust valve to be closed, and
said first exhaust valve and said second exhaust valve cooperate to limit ingress of an atmospheric gas into said vacuum manifold when no gas stream enters and is present in said first chamber or in said second chamber.

10. A method for scavenging a waste anesthetic gas component from a gas stream from an anesthetizing machine (12) comprising the steps of:
receiving said gas stream from said anesthetizing machine into a chamber (32);
detecting a presence of said gas stream received in said chamber by determining when said gas stream enters and is present within said chamber;

fluidly coupling said chamber to a vacuum manifold (16) by a selectively isolable flow path (34) in response to detection of said presence of said gas stream received in said chamber;

transferring said gas stream received in said chamber into a waste anesthetic scavenging device (22, 24, 26, 20) through said selectively isolable flow path and said vacuum manifold;

isolating said chamber from said vacuum manifold by said selectively isolable flow path when no gas stream presence is detected as being received in said chamber; and removing said waste anesthetic gas component from said gas stream by said waste anesthetic gas scavenging device; whereby said chamber and said selectively isolable flow path cooperate to minimize ingress of an atmospheric gas into said vacuum manifold when no gas stream is exiting said anesthetizing machine.

11. The method of claim 10 wherein said steps of:
detecting a presence of said gas stream received in said chamber uses a pressure sensor coupled to said chamber.

12. The method of claim 11 wherein said selectively isolable flow path includes a solenoid-actuated exhaust valve and said method further comprises the steps of:

detecting a pressure difference between a pressure in said chamber and an ambient pressure;

causing by said pressure sensor said exhaust valve to open when said pressure in said chamber is greater than said ambient pressure; and causing by said pressure sensor said exhaust valve to shut when said pressure in said chamber is not greater than said ambient pressure.

13. The method of claim 12 further comprising the step of:
actuating said exhaust valve in proportion to said pressure difference.

14. The method of claim 10 further comprising the step of:
controlling the inflow at each ingress point in a plurality of ingress points of said vacuum manifold based on a detected gas stream presence at an anesthetizing machine corresponding to said each ingress point in a plurality of anesthetizing machines corresponding to said plurality of ingress points.

15. In a healthcare facility including an anesthetizing machine (12A, 12B, 12C) having an effluent port fluidly coupled by a vacuum manifold (16) to a waste anesthetic gas scavenging system (22, 24, 26, 20) which is designed and arranged to remove a waste anesthetic gas component from a gas stream, the improvement comprising:

a chamber (32A, 32B, 32C) coupled between said anesthetizing machine and said vacuum manifold and designed and arranged to receive said gas stream exiting from said anesthetizing machine at said effluent port, said gas stream having said waste anesthetic gas component therein, a pressure sensor (40A, 40B, 40C) coupled to said chamber and designed and arranged to detect said gas stream being received into said chamber from said anesthetizing machine, and an exhaust valve (34A, 34B, 34C) coupled between said chamber and said vacuum manifold and designed and arranged to allow fluid communication therebetween only when and for as long as a pressure increase due to said gas stream exiting said anesthetizing machine at said effluent port and being received in said chamber is detected by said pressure sensor, said pressure sensor operatively coupled to said exhaust valve for control thereof.

16. The improvement of claim 15 wherein:
said pressure sensor detects said gas stream being received into said chamber from said anesthetizing machine by measuring for any difference between a pressure of said chamber and an outside ambient pressure.

17. The improvement of claim 16 wherein:
said exhaust valve is designed and arranged to provide a proportional response to any pressure difference detected by said pressure sensor such that said exhaust valve opens a small amount for a small pressure difference and said exhaust valve opens a large amount for a large pressure difference.

18. The improvement of claim 15 wherein:
said chamber and said exhaust valve cooperate to minimize ingress of an atmospheric gas into said vacuum manifold when no gas stream is exiting said anesthetizing machine at said effluent port.

19. The apparatus of claim 2 wherein:
said pressure detector determines that said gas stream including said waste anesthetic gas component enters and is present in said first chamber by measuring for any difference between a pressure of said first chamber and an outside ambient pressure.

20. The apparatus of claim 19 wherein:
said first exhaust valve is designed and arranged to provide a proportional response to any pressure difference detected by said pressure detector such that said first exhaust valve opens a small amount for a small pressure difference and said first exhaust valve opens a large amount for a large pressure difference.

* * * * *